(12) United States Patent
Telandro (10) Patent No.: US 10,729,323 B2
(45) Date of Patent: Aug. 4, 2020

(54) SYSTEM FOR MEASURING INTRAOCULAR PRESSURE

(75) Inventor: Alain Telandro, Cannes (FR)

(73) Assignee: CESACAR PARTICIPACIONS, S.L., Barcelona (ES)

( * ) Notice: Subject to any disclaimer, the term of this patent is extended or adjusted under 35 U.S.C. 154(b) by 929 days.

(21) Appl. No.: 13/266,238

(22) PCT Filed: Dec. 17, 2008

(86) PCT No.: PCT/FR2008/052328
§ 371 (c)(1),
(2), (4) Date: Apr. 17, 2012

(87) PCT Pub. No.: WO2009/081031
PCT Pub. Date: Jul. 2, 2009

(65) Prior Publication Data
US 2012/0197101 A1 Aug. 2, 2012

(30) Foreign Application Priority Data
Dec. 18, 2007 (FR) ..................................... 07 59925

(51) Int. Cl.
*A61B 3/16* (2006.01)
*A61B 5/00* (2006.01)
(Continued)

(52) U.S. Cl.
CPC .............. *A61B 3/16* (2013.01); *A61B 5/0031* (2013.01); *A61B 5/0215* (2013.01);
(Continued)

(58) Field of Classification Search
USPC ............ 600/561, 398; 606/4; 604/8; 623/4.1
See application file for complete search history.

(56) References Cited

U.S. PATENT DOCUMENTS 3,948,248 A * 4/1976 Zuckerman et al. .......... 600/457
4,722,724 A * 2/1988 Schocket .......................... 604/8
(Continued)

FOREIGN PATENT DOCUMENTS

| WO | WO-2002056758 A | 7/2002 |
|---|---|---|
| WO | WO-2004019773 A | 3/2004 |

(Continued)

OTHER PUBLICATIONS

Fingeret, Murray, "Classify corneas simply as average, thin, or thick", https://www.healio.com/optometry/glaucoma/news/print/primary-care-optometry-news, printed out on Aug. 9, 2017, 7 pages.*
(Continued)

*Primary Examiner* — Matthew Kremer
(74) *Attorney, Agent, or Firm* — Wilson Sonsini Goodrich & Rosati (57) ABSTRACT

The invention concerns a system of measuring ocular pressure, consisting of at least one implant (30) including a pressure sensor (33) and an electronic circuit (32), implanted in the cornea of an eye and an antenna (31) connected to the said circuit and implanted in the sub-conjunctival space; and a unit (50) for processing the representative values of the pressure, received by a radio-frequency link from the said electronic circuit (30).

15 Claims, 7 Drawing Sheets

(51) Int. Cl.
*A61B 5/024* (2006.01)
*A61B 5/0215* (2006.01)
*A61B 5/022* (2006.01)
*A61F 9/00* (2006.01)

(52) U.S. Cl.
CPC ....... *A61B 5/02216* (2013.01); *A61B 5/02438* (2013.01); *A61F 9/0017* (2013.01)

(56) References Cited

U.S. PATENT DOCUMENTS

| | | | | |
|---|---|---|---|---|
| 5,005,577 | A * | 4/1991 | Frenkel | 600/398 |
| 5,297,554 | A * | 3/1994 | Glynn et al. | 600/476 |
| 5,813,982 | A * | 9/1998 | Baratta | 600/398 |
| 6,186,974 | B1 * | 2/2001 | Allan et al. | 604/30 |
| 6,579,235 | B1 * | 6/2003 | Abita et al. | 600/398 |
| 7,017,404 | B1 * | 3/2006 | Kain | A61B 5/0215 73/146.5 |
| 2002/0049389 | A1 * | 4/2002 | Abreu | 600/558 |
| 2002/0151816 | A1 * | 10/2002 | Rich et al. | 600/547 |
| 2002/0177782 | A1 * | 11/2002 | Penner | A61B 5/00 600/485 |
| 2003/0078486 | A1 * | 4/2003 | Klein et al. | 600/398 |
| 2003/0078487 | A1 * | 4/2003 | Jeffries | A61B 3/16 600/398 |
| 2003/0105388 | A1 * | 6/2003 | Roy | A61B 5/0031 600/300 |
| 2003/0120200 | A1 * | 6/2003 | Bergheim et al. | 604/27 |
| 2003/0236470 | A1 | 12/2003 | Falck et al. | |
| 2004/0046936 | A1 * | 3/2004 | Iwanaga | 351/212 |
| 2004/0059248 | A1 * | 3/2004 | Messner | A61B 3/16 600/558 |
| 2004/0073137 | A1 * | 4/2004 | Lloyd et al. | 600/561 |
| 2004/0116794 | A1 * | 6/2004 | Fink | A61B 3/16 600/398 |
| 2005/0090844 | A1 * | 4/2005 | Patel | A61L 29/02 606/151 |
| 2005/0119636 | A1 * | 6/2005 | Haffner et al. | 604/500 |
| 2005/0160823 | A1 * | 7/2005 | Zdeblick et al. | 73/715 |
| 2005/0182312 | A1 * | 8/2005 | Bruce | A61B 3/16 600/399 |
| 2006/0085039 | A1 * | 4/2006 | Hastings | A61N 1/0587 607/9 |
| 2006/0136055 | A1 * | 6/2006 | Michel | 623/6.37 |
| 2007/0219632 | A1 * | 9/2007 | Castillejos | 623/6.13 |
| 2008/0208334 | A1 * | 8/2008 | Jinkerson et al. | 623/6.16 |
| 2009/0275924 | A1 * | 11/2009 | Lattanzio | A61B 3/16 604/891.1 |
| 2010/0191310 | A1 * | 7/2010 | Bly | A61B 5/0031 607/60 |

FOREIGN PATENT DOCUMENTS

| | | |
|---|---|---|
| WO | WO-2007035356 A | 3/2007 |
| WO | WO-2009081031 A2 | 7/2009 |

OTHER PUBLICATIONS

Kinshuck, David, "Corneal thickness & Intraocular Pressure (IOP)", http://www.goodhopeeyeclinic.org.uk/iopthickness.html, printed out on Aug. 9, 2017, 2 pages.*
"PCT/FR2008/052328 International Preliminary Report on Patentability dated Jun. 22, 2010".
"PCT/FR2008/052328 International Search Report (with PCT republication) dated Aug. 6, 2009".
"PCT/FR2008/052328 Written Opinion (translation) dated Aug. 6, 2009".

* cited by examiner

SYSTEM FOR MEASURING INTRAOCULAR PRESSURE

FIELD OF THE INVENTION

The present invention concerns ocular biometry in general and, more particularly, measurement of pressure in the eye.

DESCRIPTION OF EARLIER METHODS

Measurement of ocular pressure is used in the diagnosis and investigation of several diseases and to check on the efficiency of certain treatments. Measurement of ocular pressure is used in connection with diseases such as glaucoma. Arteriosclerosis, Horton's disease (temporal arthritis), diabetes, various degenerative family and hereditary pathologies, or those due to age and so on may be the subject of investigation by the analysis of the perfusion output of the head of the optic nerve.

It may be of interest to follow in real time the variations of intra-ocular pressure and the pressure of the central artery of retina for the analysis of the diseases named above.

Up to the present, intra-ocular pressure has been measured by aplanation (tonometry by aplanation) or by air-jet.

These techniques permit only occasional measurements to be made by a practitioner.

In addition, occasional measurements (spaced out in time) do not make it possible to deduce, from the pressure measured, arterial pressure at the level of the optic nerve.

A technique using corneal lenses containing an antenna and an electronic chip associated with a pressure sensor has also been described.

A drawback of using corneal lenses is that they need regular maintenance (cleaning, hydrating) by the patient. On the one hand, manipulation of these lenses by the patient runs the risk of damaging the detection and transmission circuits. On the other hand, a mistake in maintenance may falsify the measurements.

Another drawback of using corneal lenses is that it prevents the patient wearing vision corrective lenses.

These limitations mean that it is difficult to obtain a continuous measurement over a relatively long period (several days) without interruption.

Another drawback of corneal lenses is that the measurements are often highly affected by noise, which limits resolution in the possible exploitation of the measurements.

It would be desirable to be able to measure intra-ocular pressure without interruption over long periods and particularly during the night, whatever the patient's activity.

It would also be desirable to have a system of measurement available which avoids the need for the patient to do anything for the maintenance of the sensor.

It would equally be desirable to have a system of measurement compatible with the wearing of corrective lenses whatever the activity of the patient.

SUMMARY OF THE INVENTION

The invention consists of countering all or some of the drawbacks of the usual systems of measuring intra-ocular pressure.

One aim is to have in particular a system of measuring ocular pressure which obviates the use of a corneal lens.

Another aim is more particularly to have a system suitable for use by the patient during a relatively long period (several days, weeks or months).

A further aim is to retain the regular external surface of the eye, for example, to make the wearing of corrective corneal lenses possible.

To realize all or some of these aims as well as some others, a system for measuring intra-ocular pressure is proposed which includes:
  at least one implant, containing a pressure sensor and an electronic circuit, implanted in the cornea of an eye and an antenna connected to the aforesaid circuit and implanted in the sub-conjunctival space; and
  an unit for the processing the representative values of the pressure, transmitted from the aforesaid implant by a radio-frequency link.

In one way of applying the present invention, the aforesaid electronic circuit is placed in an intra-corneal cavity outside the pupillary zone, coming out at the surface of the eye by at least one slit and joined by a canal to the sub-conjunctival space for connection to the antenna.

In one way of applying the present invention, the sensor is a differential device sensing the difference in pressure between the atmospheric pressure and the intra-ocular pressure.

In one way of applying the present invention, the sensor is placed roughly equidistant from the internal and external surfaces of the cornea.

In one way of applying the present invention, unit (50) is fed remotely by the aforementioned electronic circuit.

In one way of applying the present invention, the aforesaid electronic circuit has the means to periodically transmit to the said unit a representative value of the pressure measured.

In one way of applying the present invention, the aforesaid unit has the means of comparing the representative values of the pressure with one or several thresholds.

In one way of applying the present invention, the aforesaid unit has the means of generating an alarm signal.

In one way of applying the present invention, the system also contains data processing equipment capable of communicating with the aforementioned unit.

In one way of applying the present invention, the aforesaid unit (50) has the means of deducing the arterial pulse from the values of the ocular pressure.

In one way of applying the present invention, the electronic circuit and the antenna are covered with a material biologically compatible with the nature of the cornea.

In one way of applying the present invention, the aforesaid cavity is produced by laser.

In one way of applying the present invention, the system includes two implants respectively intended for the two eyes of a person, the two implants sharing the same processing unit.

BRIEF DESCRIPTION OF THE ILLUSTRATIONS

These aims, features and advantages, as well as other matters, will be described in detail in the following account of particular methods of setting up the system given in a non-limiting manner in relation to the attached illustrations among which.

The components have been designated by the same reference numbers in the different figures.

DETAILED DESCRIPTION

Figure 1:
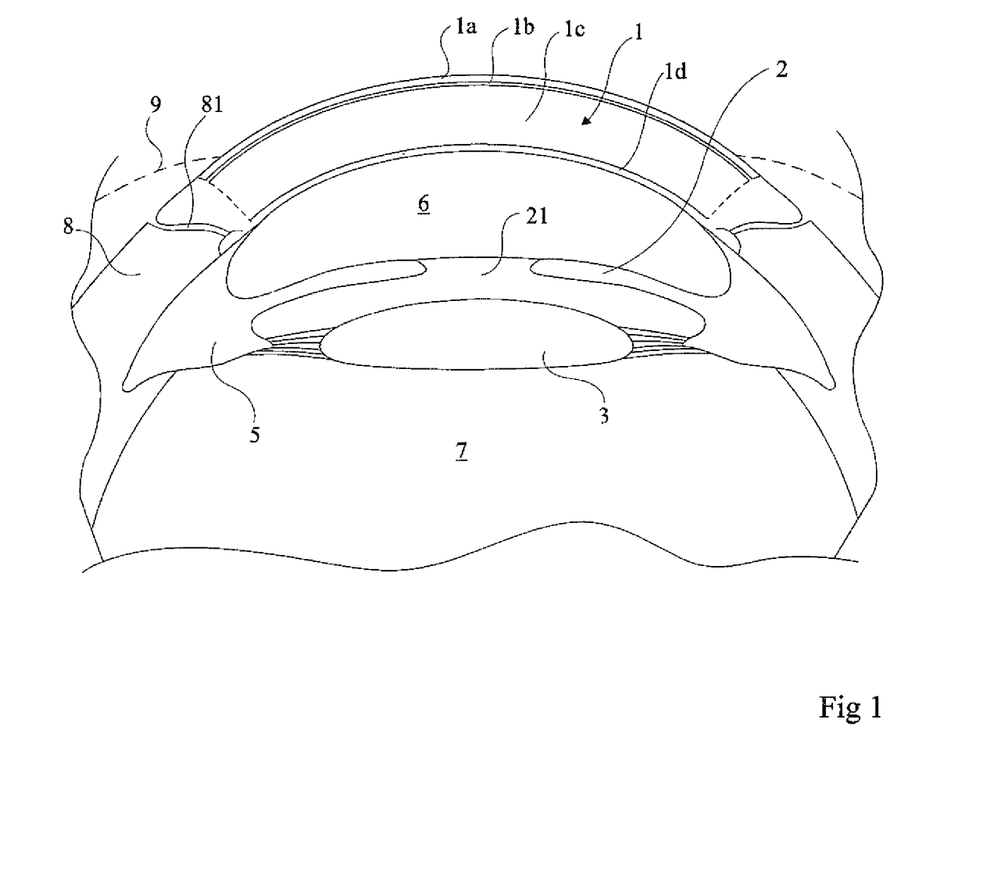
FIG. 1 is a schematic transverse section of an eye.

FIG. 1 is a diagrammatic partial transversal section of an eye which shows, at the back of the cornea 1, iris 2 and lens 3. The external periphery of the iris 2 joins the uvea 5 (the ciliary body) to which is attached the lens 3. The whole is bathed in the aqueous humor 6 (between the cornea and the lens) or the vitreous humor 7 (behind the lens). At the periphery of the cornea is the sclera 8 covered at the exterior by the conjunctiva 9 which forms the white of the eye and which stops at the periphery of the cornea. In the drawing in FIG. 1 the lacrimal canals 81 are shown between the sclera and the cornea. The pupil 21, variable in diameter and formed by the central opening of the iris 2, controls the flow of light penetrating the eye by passing through the cornea.

The cornea consists of different layers. On the outside is the corneal epithelium 1a which has a thickness of around 50 µm representing approximately $1/10^{th}$ of the total thickness of the cornea. Below it is Bowman's membrane 1b which separates the corneal epithelium from the corneal stroma 1c. The stroma 1c forms the principal layer of the cornea. Its thickness is generally between 400 and 600 µm. The inner side of the eye, the corneal endothelium 1d, gives transparency to the cornea.

According to the method of applying it, the invention requires making a cavity in the cornea in order to fit into it a pressure sensor associated with a radio-frequency transmitter (or a transmitter-receiver). This cavity is mainly created in the corneal stroma and outside the pupillary area (outside the field of vision), that it to say on a level with a part of the iris which continues to exist whatever the dilatation of the pupil. In addition, the invention requires the creation of a canal between the cavity made in the cornea and the sub-conjunctival space so as to insert a transmission antenna with an external receiver and allow the connection of the antenna to the electronic circuit sited in the cavity.

Figure 10:
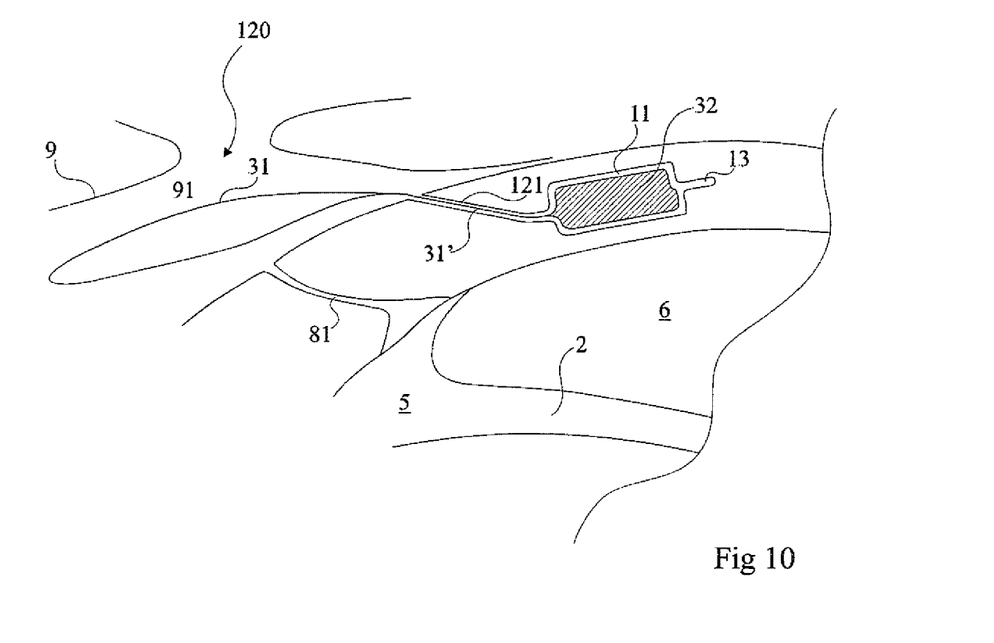
FIG. 10 is a partial sectional view of an eye fitted with a sensor and its antenna showing another method of applying the present invention.

As a variation, the sensor is introduced into the cornea from the sub-conjunctival space as will be seen in FIG. 10.

The cavity and the different openings are made by means of a laser of the type used in eye surgery operations. For example, implants (called intacts) are used to modify the curvature of the cornea in the correction of asymmetric astigmatism (keratoconus for example). In these techniques, a segment in the form of an arc in plexiglas is slid into a space created by the laser. The invention requires the use of this type of laser outside the field of vision so as not to affect the functionality of the eye. One example of laser usable is a laser producing impulses of a duration of the order of the femto-second. Such a tool is capable of making incisions in the corneal with a precision greater than 10 µm. For example, lasers available under the commercial denominations FEMTEC are suitable.

Relative to other lasers, femto-second lasers make it possible to create intra-corneal cavities without it being necessary to cut an external part away to make the part to be hollowed accessible. The precision of a femto-second laser makes it possible to vaporize only the zones buried in the cornea without destroying the upper zones. Such a laser can be programmed to make the cavity in automatic mode.

The cavity created by means of the laser in the cornea contains at least a space or housing which is intended to lodge an electronic circuit (including at least a pressure sensor and a radio-frequency emission circuit). The shapes and sizes of this housing are therefore adapted to the dimensions of the circuit to be implanted. A slit or canal connecting the housing to the outside of the eye permits the introduction of the circuit. Another slit or canal opens out between the sclera and the conjunctiva to permit the positioning of the transmission antenna. The limbic corneal-sub-conjunctival tunnel thus formed permits the passage of the ends of the antenna connected to the emission circuit.

The cavity is mainly created in the corneal stroma whose thickness is compatible with the insertion of an electronic circuit. In practice, the maximum thickness of the housing must not exceed 300 to 400 µm so as to leave at least an even thickness of at least 250 µm above the aqueous humor.

Figure 2:
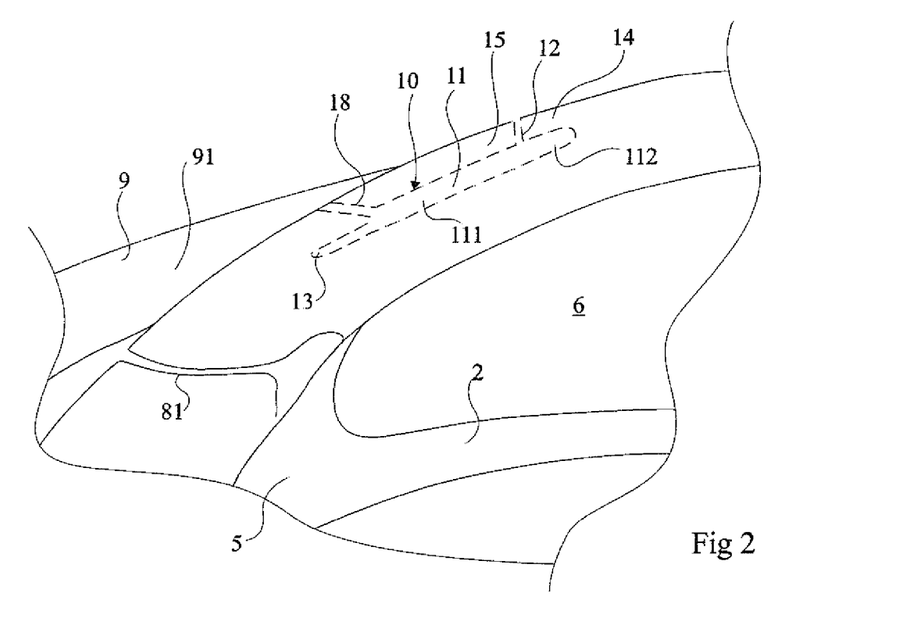
FIG. 2 represents a details of the section of FIG. 1 illustrating a stage preparatory to the fitting of an ocular implant showing a method of applying the invention.
Figure 3:
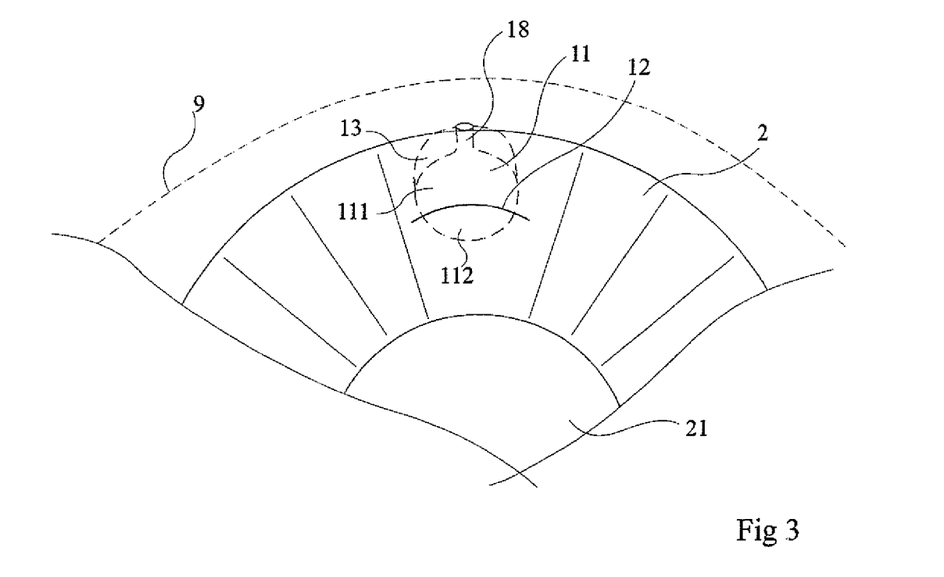
FIG. 3 is a front view corresponding to FIG. 2.

FIGS. 2 and 3 are respectively drawings in section and frontal of a part of an eye in a zone where an intra-ocular cavity 10 has been created.

The cavity 10 contains a space or housing 11 which accepts an electronic circuit (not visible in FIGS. 2 and 3) which communicates with the outside of the eye by a slit 12, straight or curved, permitting its introduction. This slit is not made at one end of the housing but in such a way that it separates the housing 11 into two parts 111 and 112. The approximately perpendicular direction at the level of the slit 112 defines the principal direction (arbitrarily longitudinal) of the cavity 10. The length of the slit 12 is preferably greater than the width of the cavity in a proportion which is a function of the thickness of the circuit to be inserted, so as to permit non-traumatizing deformation during its introduction. The cavity 11 is terminated by a space 13 for sliding or deformation useful during the positioning of the circuit. The space 13 is connected to the first part 111 of the housing, on the side of its extremity opposite slit 12. The space 13 is of a thickness less than that of the housing 11 and its length, in the main direction of the cavity 10, corresponds approximately to that of the second part 112 of the housing.

In the example of FIG. 3, housing 11 has a generally circular shape, for example, that of a disc. A femto-second laser, however, makes it possible to create an intra-corneal cavity of any shape required (for example, round, oval, parallelepiped, polygonal, disc-shaped, tubular, and so on) so as to be adapted to the shapes and dimensions of the ocular pressure sensor and its transmission circuit.

In the part of the cavity located near the outer edge of the iris, a canal 18 connects part 111 of the cavity to the sub-conjunctival space 91. This canal 18 is intended first to introduce the antenna into the sub-conjunctival space and secondly to provide the electrical connection between this antenna and the circuit contained in cavity 11.

Figure 4A:
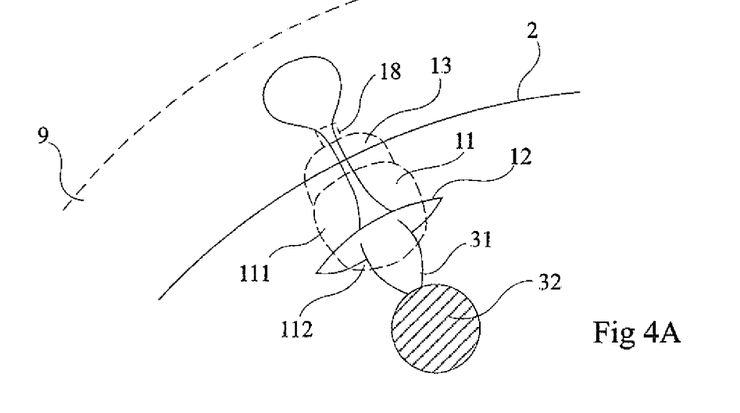
FIGS. 4A, 4B and 4C are partial schematic diagrams illustrating a method of implanting a pressure sensor and a transmission antenna.
Figure 4B:
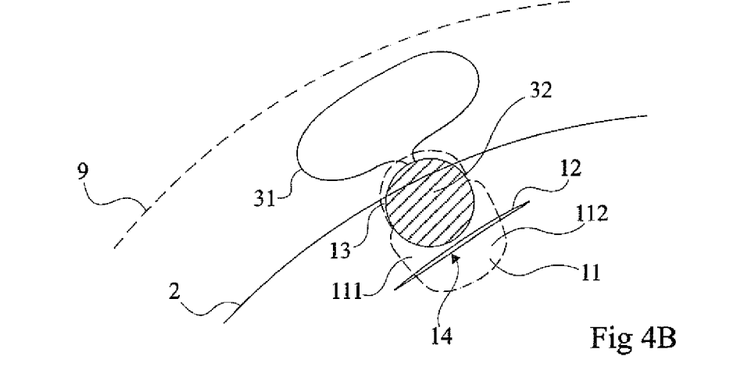
Figure 4C:
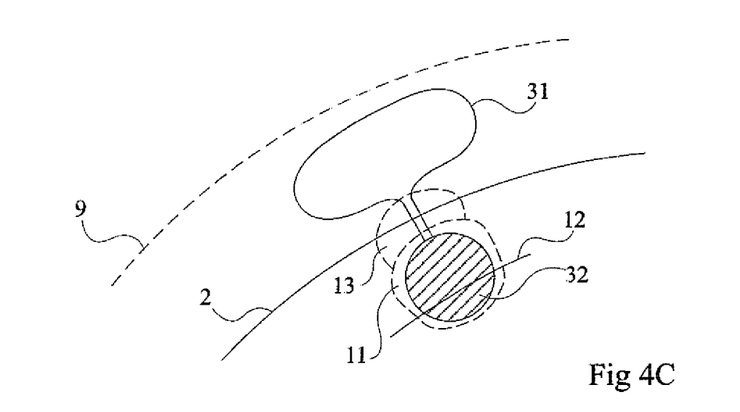

FIGS. 4A, 4B and 4C show a method of inserting an implant including an electronic circuit and an antenna in the cornea and in the sub-conjunctival space. These figures are partial frontal drawings at different stages of the insertion process. To simplify matters, only the borders of the iris 2 and of the conjunctiva 9 of the eye have been shown. It is assumed that the housing 11 is disc-shaped.

To put the implant in position, the electronic circuit 32 (shown as a disc in the figures) is previously connected to antenna 31. The circuit 32 is supposed to contain the pressure sensor or sensors. As a variation, the pressure sensor is distinct from circuit 32 while still being, for preference, contained in the same unit to be implanted in cavity 11. For example, an electronic chip 32 containing the sensor has or is within a diameter of around 3 mm and has a maximum thickness of around 200 to 250 µm. The antenna defines, for example, a conductive loop whose two ends are connected to the circuit 32. For preference, the antenna 31 and the circuit 32 (or the element containing the circuit 32 and the pressure sensor) are covered by some bio-compatible material prior to their insertion. For example, the circuit 32 is covered by plexiglas and antenna 31 is a conducting wire in a silicone sheath. The antenna 31 is preferably made in material possessing a shape memory so that it may be inserted by the canal 18 into the sub-conjunctival space and return to a loop shape once it is in position.

It is not necessary to create a space under the conjunctiva, antenna 31 being of small thickness (for example of the order of 50 µm) in relation to the circuit, it will fit by itself into the sub-conjunctival space. However, an anesthetic liquid is for preference injected into the cavity 11 (thus flowing through canal 18 in the sub-conjunctival space) before the implant is inserted. The anesthetic liquid creates a pocket by freeing adhesion. This pocket may accommodate the antenna.

FIG. 4A illustrates the beginning of the insertion of the implant. The antenna 31 is slid while being deformed from the slit 12 in the direction of the canal 18 while deforming, towards the interior of the eye, the part of the cornea located above part 112 of the housing 11. This part (14, FIG. 2), forms a sort of lip which deforms itself downwards to allow antenna 31 to pass while the part (15, FIG. 2) of the cornea above the part 111 of the housing 11 deforms itself towards the exterior. FIG. 4B shows an intermediate stage in which the circuit 32 begins to be introduced into the cavity 11. The circuit is inserted up to escaping lip 4 by entering into the sliding space 13. Then, (FIG. 4C), it is brought up under lip 14 after this latter has returned to its normal position. The circuit 32 then occupies the whole of the housing 11 and antenna 31 has resumed its shape in the sub-conjunctival space. The sliding space 13 as well as the slit 12 close.

Figure 5:
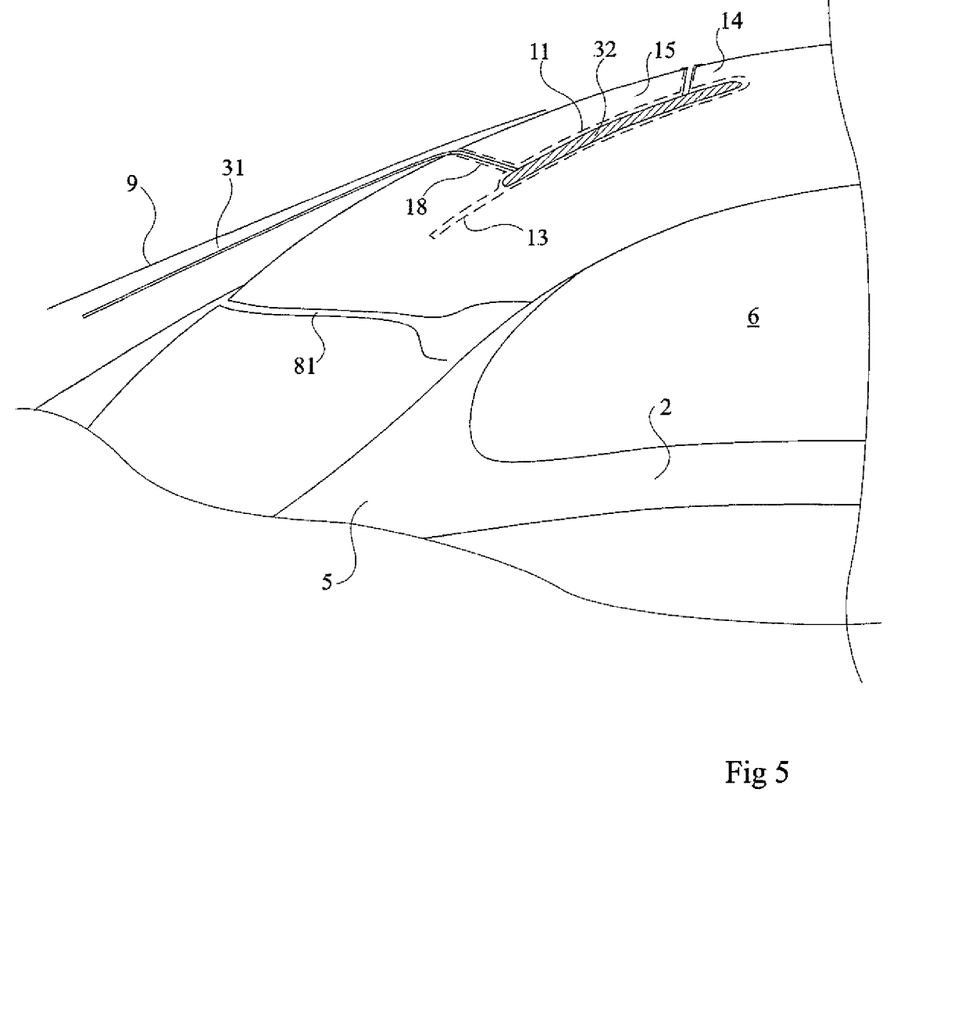
FIG. 5 is a partial section diagram corresponding to the diagram of FIG. 2 with a sensor and its antenna in position.

FIG. 5 is a drawing to be taken together with that of FIG. 3 illustrating an implant in position.

The technique suggested for the positioning of the circuit 32 and the antenna 31 does not require any stitch in the cornea in so far as the slit 12 closes without pressure.

Figure 6:
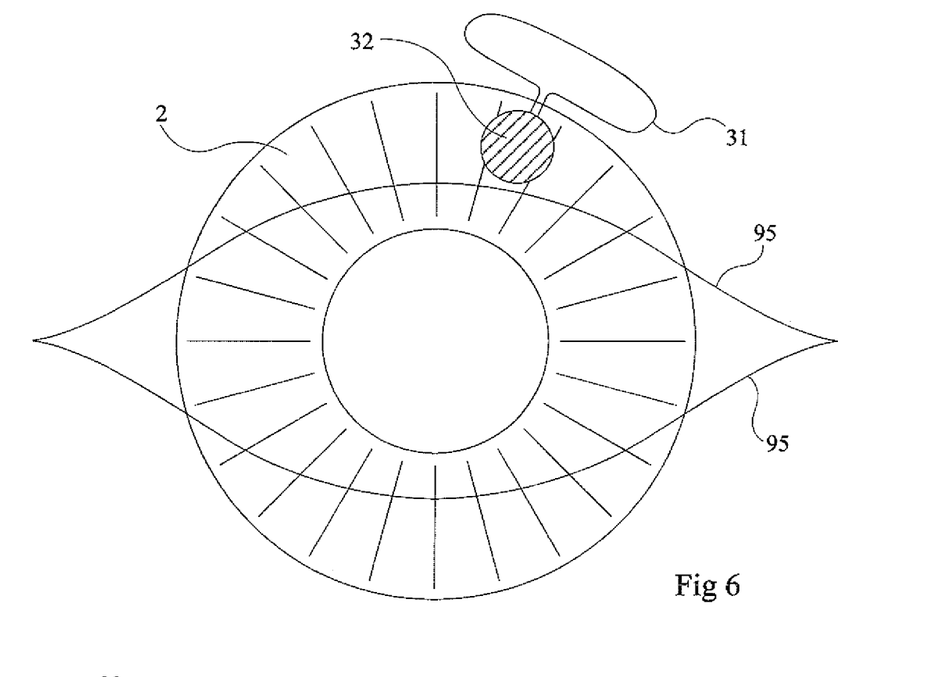
FIG. 6 is a schematic diagram of the front of an eye illustrating the sensor and its antenna in position.

FIG. 6 is a schematic frontal view of an eye illustrating the position of the chip 32 and antenna 31 according to one example of working; FIG. 6 illustrates the fact that the chip 32 is positioned outside the space useful for vision, for preference in the upper part of the eye. FIG. 6 shows the position of the eyelids 95 which brings out this absence of disturbance of the patient's vision.

Figure 7:
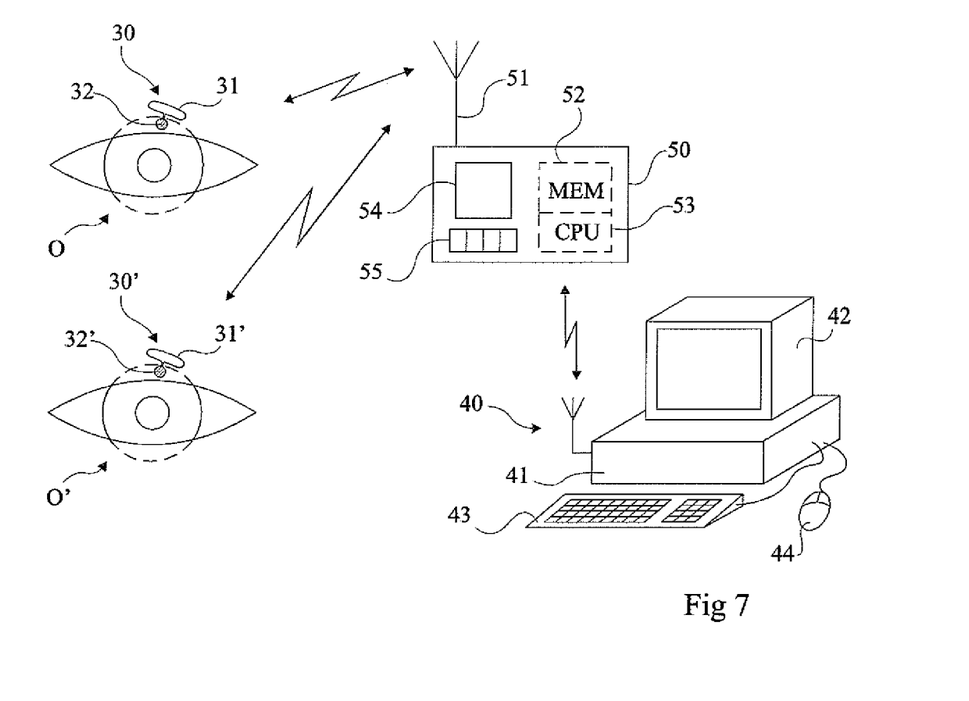
FIG. 7 shows, in a very diagrammatic manner, a method of setting up the apparatus for the measurement of intraocular pressure.

FIG. 7 is a schematic view of a system of measurement of the intra-ocular pressure showing one method of setting this up. In this example, two implants 30 and 30' (antennae 31, 31' and circuits 32, 32') of the two eyes O and O' of a patient are linked with a radio-frequency transmission-reception unit 50 which has the task of stocking or interpreting or stocking and interpreting the measurements transmitted by the implants. If required, only one eye may be fitted with an implant.

Unit 50 consists of an antenna 51 and circuits 52 (MEM) and 53 (CPU) for memorizing and processing and/or interpretation of values received from the implant and representative of the pressure measured. The transmission between the circuit 32 and the unit 50 is effected by modulation of a carrier, analogue or digital in form. The circuits of the unit 50 are, of course, adapted as necessary. The rhythm of transmission of representative values of the pressures measured depends on the application and of the possible transmission output according to the transmission-reception circuits and the frequencies used. Unit 50 also includes for preference a screen 54 and a simplified keyboard 55. This makes it possible, for example, to display instantaneous values of the pressure measured on screen 54.

The system 50 may also generate an alarm if the pressure rises above a determined value stored in the memory 52. For example, the supposed normal pressure being around 1.3 kPa to 2.7 kPa while it may vary between 0 to 10 kPa according to the disease, it is possible to predict limits adapted to the patient and his problem. It is also possible to predict the variations of ocular pressure over a given period. For example, an alarm (visual, sound or both, possibly transmitted to a remote station) may be generated if the ocular pressure varies more than more around 700 Pa during the day. It is also possible to follow variations in pressure at fixed times or as a function of external events (for example, receiving treatment, a physical activity, the ambient temperature and so on). The choice of the periodicity of the measurements (of the sampling operated by the circuit 32 of an electric signal which it receives from the pressure sensor) depends on the application and the type of the data required.

The programming of the limits is carried out for example at the level of unit 50, which simplifies the functions of the implant which has only to measure, possibly to convert, and to transmit.

A transmission in the direction unit 50 towards circuit 32 may be used to calibrate the sensor or to set its parameters, for example to enable the unit 50 to distinguish measurements from several implants, to set the periodicity of the measurements and so on.

For preference, a data-processing system (for example, a micro-computer 40 consisting of a central unit 41, a screen 42, a keyboard 43, a mouse 44 and other peripheral equipment as required) is capable of exploiting the measurements relayed by unit 50. Communication between unit 50 and the computer 40 is by wire or wireless. The micro-computer may have a processing power superior to that of unit 50. For example, the micro-computer 40 contains a program for establishing instantaneous value curves of the ocular pressure and other analytical tools (daily mean).

According to one example, circuit 32 set in the eye O contains a battery supplying it with the power required for its operation.

According to another preferred example, circuit 32 and its antenna 31 operate in the manner of an electromagnetic transponder, that is to say that the implant does not have an autonomous supply. It draws the necessary energy for its operation from a high frequency field radiated by unit 50 when it is at a short distance away (for example, around one metre). Unit 50 is then for preference contained in an object worn by the patient. It can be, for example, a object having the form of a wrist-watch, a necklace, an object worn on the belt and so on.

Figure 8:
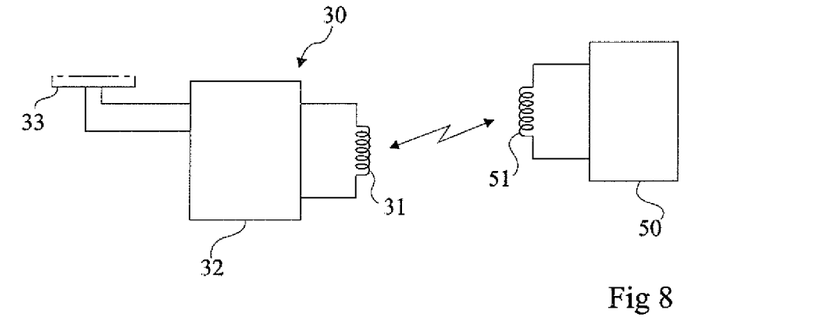
FIG. 8 is a block diagram of an implant and a receiver unit.

FIG. 8 is a simplified block diagram of such a means of implant. As regards implant 30, antenna 31 consists of the inductive element of a resonant circuit connected to an electronic circuit 32. Circuit 30 is also connected to a pressure sensor 33 (preferably integrated into circuit 32). Any pressure ordinary pressure sensor may be used provided it that it may be adapted to the range of pressures to be detected and is of small size required. For unit 50, antenna 51 is part of an oscillatory circuit excited by a high-frequency signal (for example several tens or hundreds of Mhz). This signal is capable of being modulated by unit 50 in the event of the data (for example, configuration data) having to be transmitted to the implant. Implant 30 is remotely supplied from the high-frequency carrier received by unit 50. To transmit the measurements to unit 50, the circuit 32 of the implant 30 uses, for example, a principle called retro-modulation according to which the impedance of the resonant circuit is modified in accordance with the coding of the data to be transmitted in order to modulate the charge made by the implant on the field radiated by the unit. This variations of charge is then detected by the circuits of unit 50.

The measurement of the pressure may be used to interpret the intra-ocular pressure or to deduce arterial pressure. The intra-ocular pressure which is connected to the volume of the aqueous and vitreous humor in the eye varies relatively slowly. For example, an average over several hours will be used. Besides, pressure in the eye does not depend in itself on arterial pressure, but the eye in its entirety is subject to variations in the pulse (carried by the aqueous and vitreous humors from the head of the optic nerve up to the cornea). A pressure sensor can be sufficiently sensitive to detect at the level of the cornea weak periodic variations connected to the pulse so as to deduce from them the arterial pressure of the vessels of the head of the optic nerve.

One advantage of an implant in the cornea relative to a sensor contained in a corneal lens is that the measurements are less polluted by noise. This allows a better interpretation of the ocular pressure over time.

Figure 9:
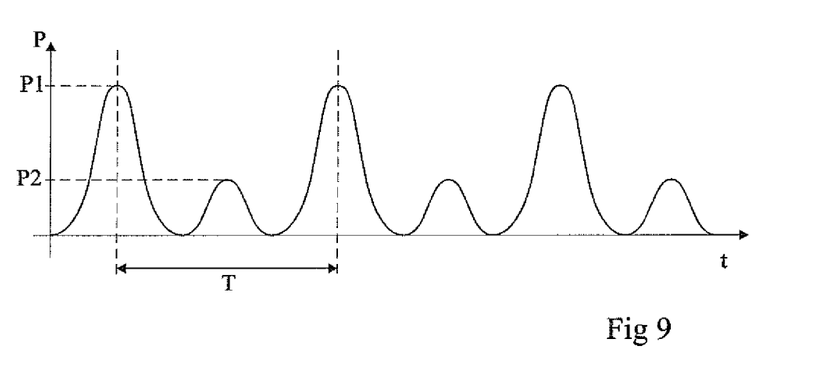
FIG. 9 shows an example of a measured curve.

FIG. 9 is a chronograph illustrating an example of variations of the ocular pressure P. According to this example, the signal/noise ratio obtained is sufficiently good for the measurements to allow to distinguish variations of pressure connected with the arterial pulse. One can in fact distinguish the peaks of pressure of amplitude P1 relatively high alternating with the peaks of amplitude P2 which are lower. The high peaks correspond to systolic pressure (contraction of the heart). The low peaks correspond to diastolic pressure (dilatation of the heart). The period T between two systolic (or diastolic) peaks enables the heart beat to be deduced.

The sensor and the antenna may be removed from the eye. The removal of the sensor and the antenna is carried out by sectioning the antenna wire of the sensor so as to free the antenna wire by pulling on one of its ends. A fibrous sheath which surrounds the antenna wire after its implantation makes this extraction easy. With regard to the sensor, a laser incision makes possible the opening of cavity 11 to free the sensor. According to the size of the sensor, it may be desired to replace this by an implant of reticulated hyaluronic acid compatible with the nature of the cornea and avoiding changing its shape. This will in particular avoid introducing astigmatism. Transparent implants in reticulated hyaluronic acid are in common use in ophthalmic surgery. They are for example used to create drainage systems in glaucoma surgery.

FIG. 10 is a sectional view to be compared with that of FIG. 5 show a variation of the invention in which the sensor is introduced into the cornea from the sub-conjunctival space.

An opening 120 is made in the conjunctiva 9 so as to make, from the sub-scleral space, a lateral entry port 121 giving access to the lodging 11 of the sensor. The sensor 32 is introduced from the port or slit 121. The wire 31' connecting to the antenna 91 placed in the sub-conjunctival space then passes through this port 121. The housing includes, as in the other methods of application, a deformation space 13 facilitating the introduction of the sensor 32.

Such a variation makes it possible to limit the traumatism by avoiding the passing of the antenna in a canal (18, FIG. 5). In addition, the direct introduction of the antenna into the sub-conjunctival space avoids the deformation or forcing of the antenna. This therefore allows wider choice of material (for example, one may use a gold wire which may be too fragile to be deformed with no risk in order to pass it into the canal 18). In this variation, the corneal surface remains intact.

Figure 11:
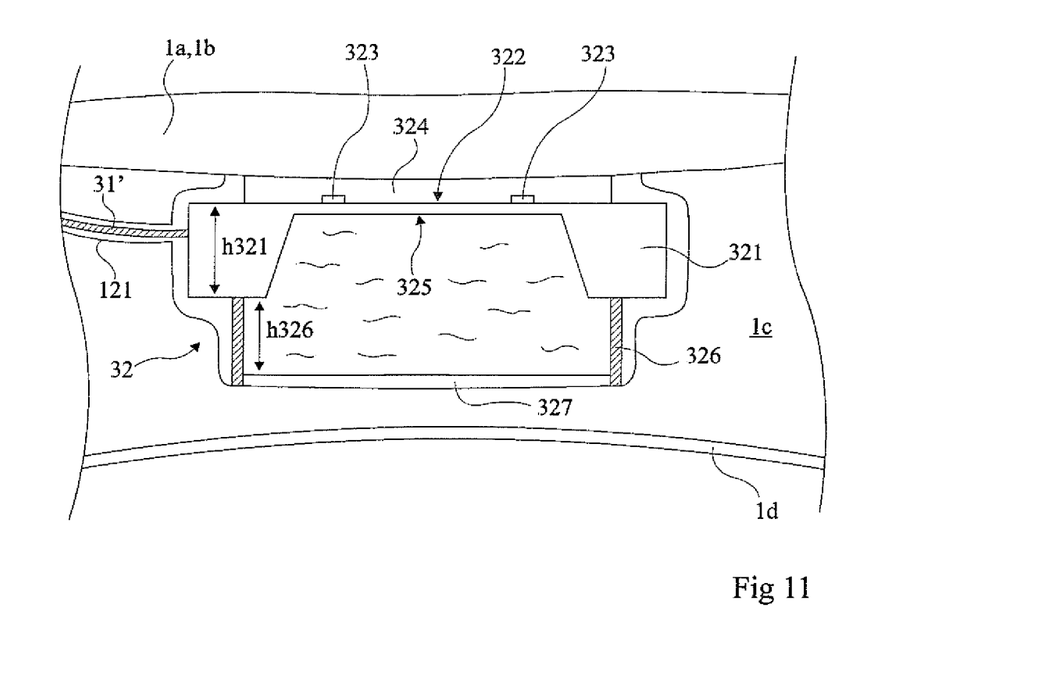
FIG. 11 is a sectional view of a detail at the level of the sensor of FIG. 10.

FIG. 11 is a sectional view of an example of a pressure sensor which can be implanted in the cornea in one way of applying the invention. This sensor is a piezo-resistive pressure sensor with a radio-frequency link. The sensor is a differential sensor, containing a device 321 measuring a difference of pressure between its two faces. The front face 322 of the device 321 contains piezo-electric elements or stress gages to which is attached a flexible electrically isolating membrane 324 (for example in acrylic or silicone material). The rear face 325 of device 321 is in contact with a neutral liquid (without electrical charge), for example a physiological serum, contained in a chamber 326 whose bond is formed by a membrane 327. The housing 11 is made in the corneal stroma 1c so that the membrane 324 is as close as possible to the surface of the cornea, that is to say the epithelium 1a while remaining under Bowman's membrane 1b, and that the membrane 327 is as close as possible to the endothelium 1d. The sensor thus measures the difference between the intra-ocular pressure and the atmospheric pressure.

A differential measurement is more reliable. In fact, the measurement becomes independent of exterior parameters. In addition, this makes possible the deduction of the arterial pulse from the measurements of the ocular pressure.

To optimize the measurement, the sensor is roughly equidistant from the internal and external surfaces of the cornea. Care should also be taken to ensure that the thickness of the existing cornea on both sides should be at least 100 µm and that the same thickness should be present on both sides. As a particular example of application, the thickness h321 of a peripheral framework of the measuring device 321 is approximately 200 µm while its sensitive central part is of a thickness of about 10 µm. The membrane 324 has a thickness of about 20 µm. The height h326 of the chamber 326 transmitting the pressure to the right of the framework of the measuring device is about 200 µm. This height may be modified with respect to the thickness of the corneal stroma 1c.

Figure 12:
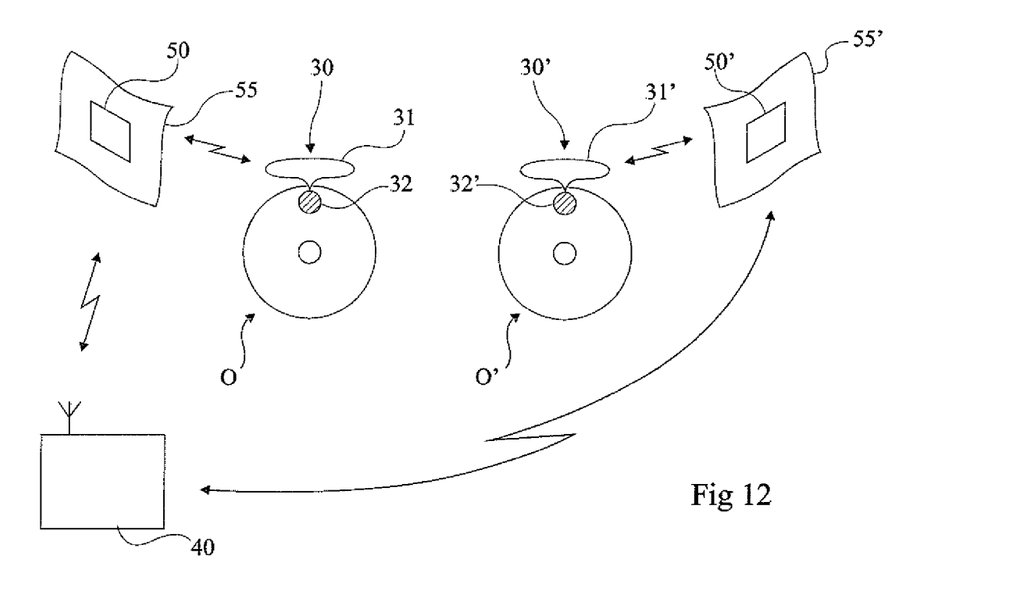
FIG. 12 shows, in a very schematic way, a variant of the system in FIG. 7.

FIG. 12 shows, in very schematic fashion, a variation of the system described above with regard to FIG. 7. In this variant, each implant (in the example of FIG. 12, each eye O, O' is fitted with an implant 30, 30', and each implant is linked to a radio-frequency transmitter-receiver circuit 60, 60', for example the Bluetooth type positioned a short distance away. Each circuit 60, 60', is, for example mounted on a patch 65, 65', stuck to the temple of the patient or on to the frame of a pair of glasses. As in the method of application of FIG. 8, the implants 30 and 30' are remotely fed by the circuits 60 and 60'. The circuits 60 and 60' have the function of receiving the measurements transmitted by the sensors 32 and 32' and forwarding them on to a storage and/or interpretation device, for example, a unit 50 of the type shown in FIG. 7 or directly to a more sophisticated item of equipment 40. For example, unit 50 or item of equipment 40 may be a laptop computer, a mobile telephone, a wristwatch and so on.

One advantage of recourse to short-range circuits 60 and 60' to serve as transmission relays between the sensors and the analytical system is that it limits the power of these circuits 60 and 60'. In this way the risks of over-heating in the corneal sensor and of interference with other apparatus is avoided.

One advantage of the invention is that it retains the appearance of the surface of the eye and does not form any excrescence relative to the surface of the cornea. It is compatible with the wearing of a corneal lens, particularly corrective.

Another advantage is that contrary to the use of a lens, the sensor does not require maintenance.

Another advantage is that it makes it possible to choose the angular position in which the intra-ocular pressure sensor is placed. This may permit, for example, having several sensors in the periphery of the eye, for example, for a measurement of the field of variation of the pressure.

Another advantage is the reversible aspect of the placing of the sensor in the intra-corneal space.

Particular methods of using the present invention have been described. Several variants and modifications will appear to the specialist. In particular, the practical employment of the invention and in particular the production of the electronic circuits is within the capacities of the specialist using the functional details given above and the respective functionalities required for implant 30, unit 50 and computer 40. For example, electronic circuit 32 includes only pressure sensor 33 and a data transmission system leading to unit 50. According to another example, sensor 33 and circuit 32 are of the same type as those included in ordinary intra-corneal lenses. Similarly, the choice of communication techniques between implant 30 and unit 50, then, if need be, between this unit and a micro-computer 40 is within the capacities of the specialist as a function of non-traumatizing techniques available, compatible with the limitations imposed by lack of space. In particular, the choice of transmission frequencies as a function of the standards and frequencies, and the choice of the power or powers of transmission (particularly remote supply) so as not to harm the eye are within the capacities of the specialist. Besides, the use of a laser, its parametrization or programming for the employment of the invention have not been given in detail, as they are within the capacities of the specialist trained in the use of such a laser. In practice, a local anesthetic is used during the siting of the system (creating of the cavity and positioning of the antenna and the sensor). Finally, various methods of production and variations may be combined.

The invention claimed is:

1. A system for monitoring an eye pressure, comprising:
   (1) an implant comprising:
      (a) a pressure sensor configured to be implanted in between an internal surface and an external surface of a cornea of an eye, wherein the pressure sensor comprises a first pressure sensor surface and a second pressure sensor surface, wherein an electrically neutral liquid is between the first surface and the second surface, wherein the pressure sensor is configured to sense an intraocular pressure that is transmitted to the internal surface of the cornea with the first pressure sensor surface and sense an atmospheric pressure that is transmitted to the external surface of the cornea with the second pressure sensor surface, and wherein the pressure sensor is configured to determine the eye pressure which is equal to a difference between the intraocular pressure that is transmitted to the internal surface of the cornea and the atmospheric pressure that is transmitted to the external surface of the cornea; and
      (b) a first antenna operatively connected to the pressure sensor and configured to be implanted in a sub-conjunctival space of the eye and to transmit a signal that indicates the eye pressure; and
   (2) a unit comprising a second antenna and a processor, wherein the second antenna is configured to receive the signal, and wherein the processor is configured to process the signal.

2. The system according to claim 1, in which the pressure sensor is configured to be placed in an intra-corneal cavity outside a pupillary zone, coming out at a surface of the eye by at least one slit and joined by a canal to the sub-conjunctival space for connection to the first antenna.

3. The system according to claim 1, in which the pressure sensor is configured to be placed equidistant from the internal and the external surfaces of the cornea.

4. The system according to claim 1, in which the signal comprises a radio-frequency signal.

5. The system according to claim 1, in which the unit remotely supplies energy to power the pressure sensor.

6. The system according to claim 1, in which the first antenna periodically transmits to the signal to the unit.

7. The system according to claim 1, in which the unit compares the eye pressure with one or several thresholds.

8. The system according to claim 7, wherein the unit generates an alarm signal.

9. The system according to claim 1, further comprising data processing equipment capable of communicating with the unit.

10. The system according to claim 1, in which the unit is configured to determine an arterial pulse from the eye pressure.

11. The system according to claim 1, in which the pressure sensor and the first antenna are covered with a material biologically compatible with the cornea.

12. The system according to claim 1, in which the pressure sensor is configured to be placed in an intra-corneal cavity produced by a laser outside a pupillary zone, coming out at a surface of the eye by at least one slit and joined by a canal to the sub-conjunctival space for connection to the first antenna.

13. The system according to claim 1, comprising two implants respectively intended for two eyes of a person, the two implants sharing the unit.

14. The system according to claim 1, wherein the pressure sensor is a piezo-resistive pressure sensor with a radio-frequency link.

15. The system according to claim 1, wherein the first antenna is operatively connected to the pressure sensor by a wire.

* * * * *